United States Patent [19]
Palma et al.

[11] Patent Number: 5,344,443
[45] Date of Patent: Sep. 6, 1994

[54] HEART PUMP

[75] Inventors: Rodolfo Palma, Troy; William H. Miller, Loudonville, both of N.Y.

[73] Assignee: REM Technologies, Inc., Schenectady, N.Y.

[21] Appl. No.: 946,381

[22] Filed: Sep. 17, 1992

[51] Int. Cl.[5] .................. A61M 1/10; A61N 1/362
[52] U.S. Cl. ........................................ 623/3; 600/16
[58] Field of Search .................. 600/16, 17; 623/3; 417/356, 413 R; 416/111

[56] References Cited

U.S. PATENT DOCUMENTS

| | | | |
|---|---|---|---|
| 1,632,357 | 6/1927 | White. | |
| 2,171,460 | 8/1939 | Thrasher | 103/87 |
| 3,433,163 | 3/1969 | Sheets et al. | 103/87 |
| 4,105,016 | 8/1978 | Donovan, Jr. | 128/1 D |
| 4,155,022 | 5/1979 | Crockett | 310/168 |
| 4,173,796 | 11/1979 | Jarvik | 3/1.7 |
| 4,382,199 | 5/1983 | Isaacson | 310/87 |
| 4,617,726 | 10/1986 | Denk | 29/598 |
| 4,625,712 | 12/1986 | Wampler | 128/1 D |
| 4,688,998 | 8/1987 | Olsen et al. | 623/3 X |
| 4,753,221 | 6/1988 | Kensey et al. | 128/1 D |
| 4,763,032 | 8/1988 | Bramm et al. | 623/3 X |
| 4,779,614 | 10/1988 | Moise | 623/3 X |
| 4,846,152 | 7/1989 | Wampler et al. | 600/16 |
| 4,864,176 | 9/1989 | Miller et al. | 310/194 |
| 4,908,012 | 3/1990 | Moise et al. | 600/16 |
| 4,919,647 | 4/1990 | Nash | 600/16 |
| 4,944,748 | 7/1990 | Bramm et al. | 623/3 |
| 4,994,078 | 2/1991 | Jarvik | 623/3 |
| 5,001,378 | 3/1991 | Miller et al. | 310/178 |
| 5,006,748 | 4/1991 | Wintermute | 310/258 |
| 5,055,005 | 10/1991 | Kletschka | 623/3 X |
| 5,078,741 | 1/1992 | Bramm et al. | 623/3 |
| 5,195,877 | 3/1993 | Kletschka | 623/3 X |
| 5,286,176 | 2/1994 | Bonin | 417/413 R |

OTHER PUBLICATIONS

J. Orth, M. Isaacson, K. Carr, S. Nielsen, and R. Jarvik; "An Electronically Commutated Brushless DC Motor Applied to a Total Artificial Heart", Conference: Procdeedings of the First Annual International Motorcon '81 Conference. Chicago, Ill., pp. 667–676, Jun., 1981.
Derwent's abstract, No. 85-42926/07, week 8507, Abstract of SU, 1101237 (MOSC Phys-Tech Inst), Jul. 7, 1984.
Derwent's abstract, No. 90-176654/23, week 9023, Abstract of SU, 1500310 (Kiselev Yu M), Aug. 15, 1989.

*Primary Examiner*—Randall L. Green
*Assistant Examiner*—Elizabeth M. Burke
*Attorney, Agent, or Firm*—Heslin & Rothenberg

[57] ABSTRACT

A heart pump having a housing with a central longitudinal axis, inlet means and an outlet means is disclosed. A stationary shaft extends axially within the housing and the means are provided for supporting the shaft centrally located within the housing. A stator assembly is mounted about the stationary shaft and a shell assembly is rotatable about the stator assembly and shaft. The shell assembly is located between the housing and stator assembly and includes a spiral ridge located on the outerside thereof for pumping blood through the housing between the housing and shell assembly as the shell assembly rotates. Rotor laminations are located on an innerside of the shell assembly. The rotor laminations have a plurality of axially extending permanent magnets therebetween which are circumferentially spaced about the stationary shaft. A damper winding means is mounted within the rotor laminations. Blood may flow between the shell assembly and housing without exposure to magnetic fields.

22 Claims, 6 Drawing Sheets

HEART PUMP

BACKGROUND OF THE INVENTION

This invention relates to the field of pumps, and more particularly, to a heart pump useable for pumping blood.

Various different heart pumps have been used to pump blood through a human body. Pulsatile blood flow, simulating actual blood flow as provided by the heart, is more easily produced using a piston type heart pump. However, pulsatile blood flow may also be produced by a centrifugal heart pump powered by an electric inverter. Certain heart pumps have been designed for use as artificial or substitute hearts to be either implanted within a body, or mounted subcutaneously to pump blood throughout the body.

As an alternative to the substitute artificial heart, various cardiac assist pumps, designed to be mounted subcutaneously in conjunction with a weak existing heart, have been developed. The purpose of assist devices is to alleviate and/or minimize stress in a patient's natural heart without sacrificing overall pumping ability. The centrifugal heart pumps which have been used as cardiac assist devices include miniature motors which are mounted intravascularly between the left ventricle and aorta artery, between ventricles, within the heart itself or within the femoral aorta artery.

For example, U.S. Pat. No. 4,105,016 to Donoran discloses a heart pump which is mountable in parallel relationship with a ventricle and is run at a constant speed. The pump automatically operates when the pressure within the ventricle reaches a predetermined value. U.S. Pat. Nos. 4,265,712 and 4,846,156 to Wampler disclose a high capacity intravascular blood pump utilizing percutaneous access which may be inserted into the heart through the femoral artery and driven via a flexible cable from an external power source. Also, U.S. Pat. No. 4,173,796 to Jarvik discloses a circulatory assist device which may be mounted between the left ventricle and right ventricle. These pumps are essentially centrifugal pumps which utilize conventional impellers and/or rotors to pump blood.

Since these centrifugal cardiac assist pumps typically require bearings and seals, it is desirable to develop a heart pump which minimizes the use of such bearings or seals and therefore provides greater reliability during use. Also, since intravascular heart pumps are designed to minimize stress on the heart, it is desirable to utilize a heart pump which can operate for a maximum period of time without failure.

One potential problem with centrifugal rotor and impeller type pumps may be that they damage blood cells as the blood cells pass through the rotor or impeller. The extreme pressure differential across rotors or impellers may cause the explosive decompression and cavitation, etc of blood cells. It is therefore desirable to develop a heart pump which will minimize damage to blood cells being pumped therethrough.

Another problem with conventional heart pumps including heart assist devices is that their pumping rates cannot be varied adequately to mimic a healthy heart. As the heart becomes weakened, its ability to increase its pumping rate becomes diminished. Typical induction motors used as heart assist devices are inherently difficult to modulate so as to precisely control the rotation thereof. It is therefore desirable to achieve a heart pump which will be capable of producing a pulsatile flow and also be capable of creating a variable pumping rate.

The pump disclosed in U.S. Pat. No. 4,688,998 includes a magnetically suspended and rotated impeller pump which may be connected between the heart and the aortic arch. The impeller is magnetically suspended and rotated and a valve may be included as part of the impeller to prevent reverse flow if the pump is used as a ventricle assist device. Another magnetic-type heart assist device, disclosed in U.S. Pat. No. 4,779,614 to Moise, may allow for greater blood flow. This axial flow blood pump utilizes neodymium-boron-iron rotor magnets which allow a substantial gap between the static motor armature and the rotor. Therefore, greater blood flow may be induced as compared to conventional magnetically suspended rotor impeller pumps.

One potential problem with both magnetic and other conventional types of heart pumps including assist devices, is that the flow of blood therethrough crosses an intense magnetic field. The full effects of the magnetic field upon blood cells are unknown. However, the effects of low level electro-magnetic radiation upon the human body have been questioned. Therefore, heart pumps which allow blood to flow through intense magnetic and/or electromagnetic fields may not be desirable.

Accordingly, it is desirable to achieve a heart pump in which blood flowing therethrough does not intercept a magnetic field. It is also desirable to develop a centrifugal subcutaneously mountable heart pump and/or heart assist device which may be precisely controlled so as to more adequately mimic the performance of a normal heart and create variable pulsatile flow. Moreover, it is desirable to develop a heart pump and assist device, which utilizes a synchronous AC motor while minimizing damage to blood cells pumped therethrough. The pump should be capable of being intravascularly attached between a ventricle of the heart and an artery.

SUMMARY OF THE INVENTION

The aforementioned objects and advantages may be achieved through implementation of the heart pump in accordance with the principles of the present invention.

In accordance with these principles, the heart pump may include a housing having an inlet means and outlet means; a stationary shaft extending axially within the housing; means for supporting the shaft within the housing; a stator assembly mounted about the stationary shaft; a shell assembly rotatable about the stator assembly and stationary shaft; and a means for generating a magnetic field to rotate the shell assembly. The magnetic field may be generated between the stator assembly and shell assembly such that the magnetic field does not cross the area between the shell assembly and housing. Accordingly, blood flow between the shell assembly and housing will not intercept the magnetic field.

The shell assembly is located between the housing and stator assembly and may include a means for pumping blood. The means for pumping blood may be a spiral ridge located on an outerside thereof between the housing and shell assembly as the shell assembly rotates. The means for creating a magnetic field between the stator assembly and shell assembly includes rotor laminations located on an inner side of the shell assembly, and damper winding means mounted within the rotor laminations. The rotor laminations may have a plurality of axially extending permanent magnets therebetween which are circumferentially spaced about the stationary shaft. To insure that the magnetic field does not enter the area between the shell assembly and housing, where blood will flow, a flux shield may be placed on the inside of the shell assembly to restrict the magnetic field therein.

The means for supporting the shaft centrally within the housing may include one or more spiders. The heart pump may also include means for supplying power to the stator assembly. The stator assembly may include a plurality of stator core laminations surrounding the stationary shaft. The stator core laminations may form a plurality of axially extending slots circumferentially spaced about the stationary shaft. The stator assembly may also include a plurality of stator windings located within the axially extending slots formed by the stator core laminations.

The axially extending permanent magnets of the shell assembly which are circumferentially spaced about the stationary shaft have magnetic poles facing in a tangential direction whereby sides of adjacent permanent magnets oriented about the circumference facing each other have identical polarities.

The damper winding means may include a plurality of damping bars which extend axially within the rotor laminations of the shell assembly and are spaced circumferentially about the stationary shaft. Also, the damper winding means may include one or more shorting rings circumferentially spaced about the stationary shaft and/or damping slats. The shorting rings may contact the damping bars and damping slats so as to be in electrical conductive relationship therebetween.

The shell assembly may be supported by bearings at the first and second ends of the stationary shaft by bearings such as jewels bearings.

The stator windings receive three phase power such that each of the windings will have one of three phases of power transmitted thereto- The means for supplying power to the three phase windings may comprise a passage extending within the stationary shaft leading from the stator assembly.

The heart pump may be intravascularly mounted between a ventricle and an artery, or mounted between the left ventricle and the aorta artery to be used as an assist device.

BRIEF DESCRIPTION OF THE DRAWINGS

These and other objects, advantages and features of the present invention will be more readily understood from the following detailed description, when considered in conjunction with the accompanying drawings in which.

DETAILED DESCRIPTION

Figure 1:
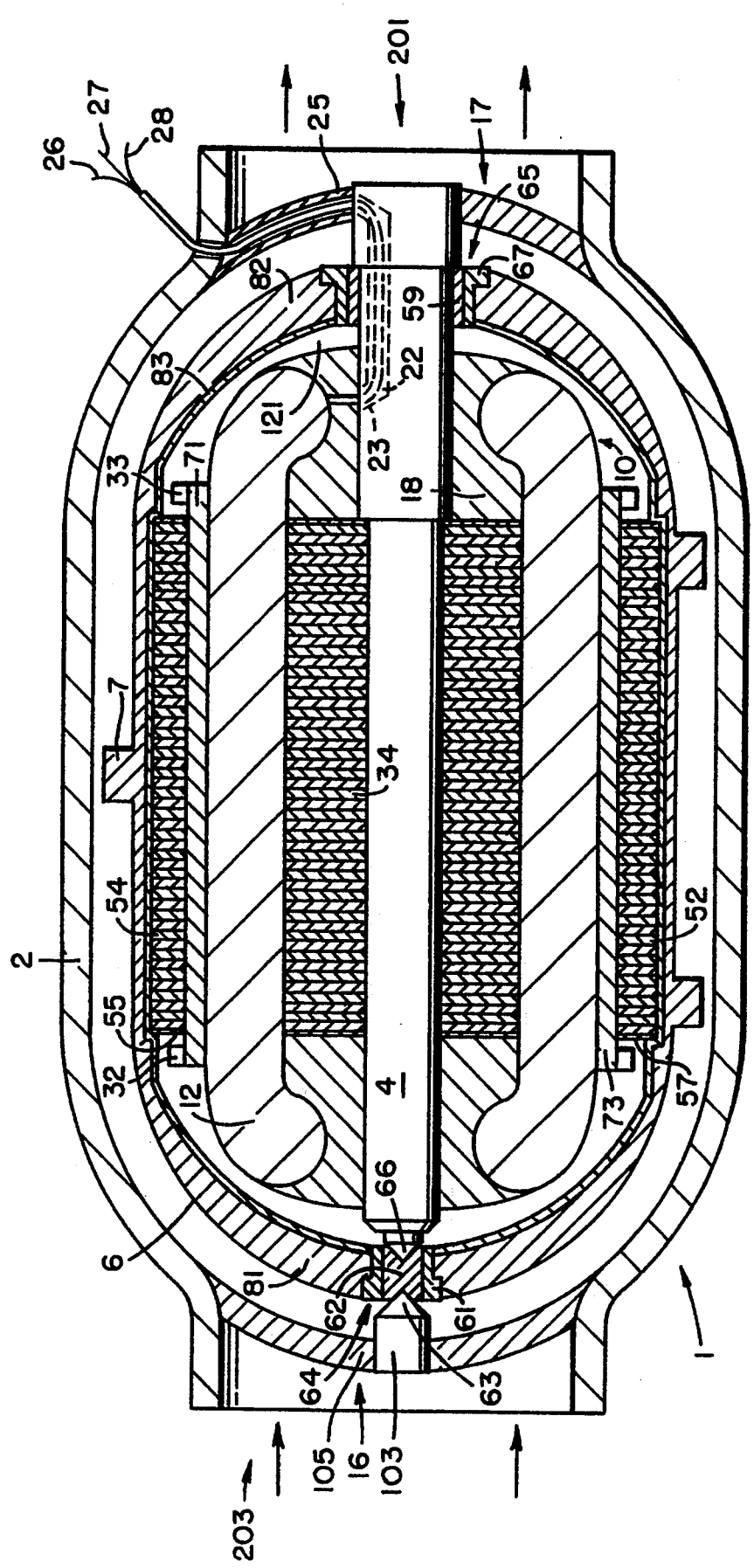
FIG. 1 is a cross-sectional view from the side of one embodiment of the heart pump constructed in accordance with principles of the present invention.

In FIG. 1, a heart pump, generally denoted 1 and constructed in accordance with the principles of the present invention, is shown. The pump 1 includes a housing 2, having an outlet means 201 and an inlet means 203, surrounding a stationary shaft 4 extending axially therein, and a stator assembly 10 affixed to the shaft 4. A shell assembly 6, containing a spiral ridge 7 thereon, surrounds the stator assembly 10 and is capable of rotating relative to the housing 2 and stator assembly 10. The stator assembly 10 and stationary shaft 4 are mounted within the housing 2 by means of a pair of spiders 16, 17 which effectively center the stationary shaft 4 and stator assembly 10 within the housing 2.

In this description, the terms axial, circumferential and radial are used to describe directions relative to a central axis concentric with the stationary shaft 4. Unlike conventional brushless motors, the shaft 4 does not rotate, but instead supports the stator assembly 10. The stator assembly 10 contains a plurality of stationary stator laminations 34 which include individual disk shaped laminates bonded together, i.e., stacked, in the axial direction as is well known in the art. The stator laminations 34 are configured such that a plurality of slots or passages 36 (shown in FIG. 2) extend axially throughout their length. The slots or passages 36 are spaced circumferentially about a central axis concentric with the stationary shaft. The slots 36 support stator windings 12, which extend axially therein, and are circumferentially spaced about stationary shaft 4. The ends of the stator windings 12 overlap the shorter stator laminations 34. An inert solid material 18 may be used to fill the area between the stationary shaft 4 and stator windings 2 not occupied by the stator laminations 34.

Figure 2:
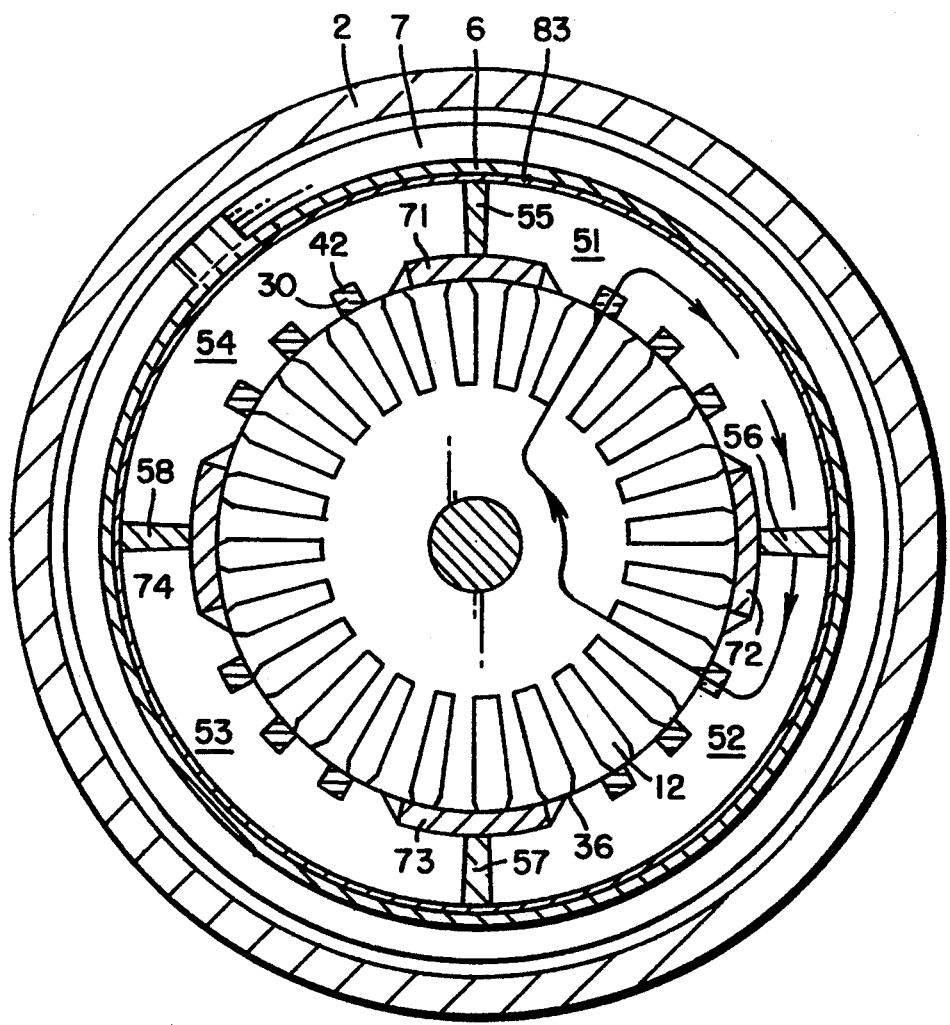
FIG. 2 is a cross-sectional view from the axial direction of the heart pump depicted in FIG. 1 constructed in accordance with the principles of the present invention including a representation of a magnetic flux pattern existing between the stator assembly and shell assembly.

FIGS. 1 and 2 depict a three phase motor. However, the invention is not limited to a three phase motor and other numbers of phases may be used in accordance with the present invention. The stator windings 12 are supplied with power from an external power supply (not shown). In a three phase motor, each of the stator windings 12 will have one of the three phases of current, i.e., phase A, B or C, flowing therethrough. Each stator winding 12 contains a plurality of electrical conductors which are typically wound in a spiral-like pattern, as is well known in the art. For convenience, each winding 12 is wound in the same axial direction. As in conventional dynamoelectric machines, each phase of current may be fed into the stator assembly 10 by a conductor which is connected to only one of the windings 12. The windings are connected, however, such that each winding (having one particular phase of current running therethrough) is surrounded by two windings (one on each side) such that consecutive windings have different phases of current running therethrough. Accordingly, the windings 12 are oriented such that consecutive circumferentially spaced windings contain, for example, representative current phases: A, B, C, A, B, C . . . flowing therethrough. This particular configuration for armature windings in dynamoelectric machines is well known in the art. To supply power to the windings 12, the stationary shaft 4 may contain a passage 22 which extends axially therethrough leading from an opening 23 near the windings 12 to a passage 25 within the second spider 17 which leads to the area outside the housing 2. Other techniques for supplying power to the stator assembly 10 may also be used and the invention is not limited to any one particular technique.

The heart pump contains a means for creating a magnetic field to rotate the shell assembly. The magnetic field is created between the stator assembly 10 and the shell assembly 6 and may not cross the area between the shell assembly 6 and housing 2 where blood will flow. The means for creating a magnetic field may include a plurality of rotor laminations 51, 52, 53, 54 and a damper winding means. Affixed to the rotatable shell assembly 6, are the axially extending rotor laminations 51, 52, 53, 54, each shown in FIG. 2. Although four rotor laminations are suggested, a different number of rotor laminations could conceivably suffice. The rotor laminations are arcuately shaped in cross section and are mounted about the circumference of the stator laminations 34 so as to be aligned therewith. Because of their arcuate shape, the rotor laminations 51–54 encircle the stator assembly at close clearance and tolerance.

Figure 5:
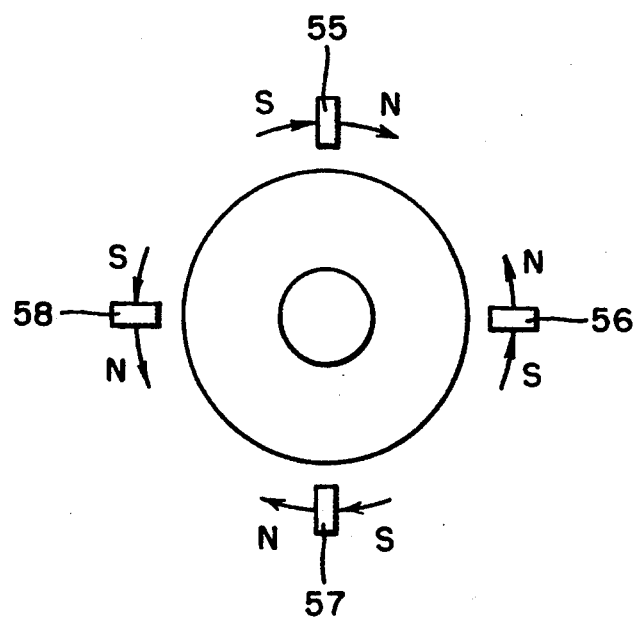
FIG. 5 is a schematic representation of an axial view of the orientation of the permanent magnets incorporated into the heart pump in accordance with the principles of the present invention.

Permanent magnets 55, 56, 57, 58 are mounted between adjacent pairs of the rotor laminations. Rather than being radially or axially oriented, the magnetic poles of the permanent magnets 55, 56, 57, 58, are tangentially oriented. However, the polarities of the magnets should alternate such that circumferentially facing sides of neighboring permanent magnets have identical polarities, as shown in FIG. 5. Referring to FIG. 5, permanent magnet 55 has a north/south polarity oriented clockwise. Permanent magnet 56 has a north/south polarity oriented counter clockwise, permanent magnet 57 has a north/south polarity oriented clockwise, and permanent magnet 58 has a north/south polarity oriented counter clockwise. The result being that the circumferential areas between permanent magnets have a magnetic flux caused by identical but oppositely directed magnetic fields.

As shown in FIG. 2, the rotor laminations 51–54 contain a plurality of axially extending grooves or passages 42 on the inside diameter thereof. The damper winding means includes damping bars 30, which may be comprised of an electrically conductive non-magnetic material such as copper, aluminum, etc., extending axially through the passages 42. The damping bars 30 may be press fit in the passages 42 or secured within the lamination by the shape of the passages 42. However, other means for securing the damping bars may suffice. Located below the permanent magnets 55, 56, 57, 58, and within cutout sections which may exist in the lower sides of the rotor laminations 51–54, are damping slats 71, 72, 73, 74. The damping slats 71–74 extend axially, approximately the length of the rotor laminations 51, 52, 53, 54, and are circumferentially spaced between the permanent magnets 55, 56, 57, 58 and stator assembly 10. The damping slats 71–74 are also made of an electrically conductive non-magnetic material such as copper, aluminum, etc. A pair of shorting rings 32, 33 (FIG. 1) each located at axially opposite ends of the rotor laminations, may be in contact with the damping bars 30 and/or damping slats 71–74 thereby placing the shorting rings 32, 33 at the same potential as the damping bars 30 and damping slats 71–74. The shorting rings 32, 33 encircle the stator assembly, as shown in FIG. 1. The stator laminations 34 may be fastened to the stationary shaft 4 and the rotor laminations fastened to the rotatable shell 6. However, other techniques for affixing these structures may suffice.

Figure 6:
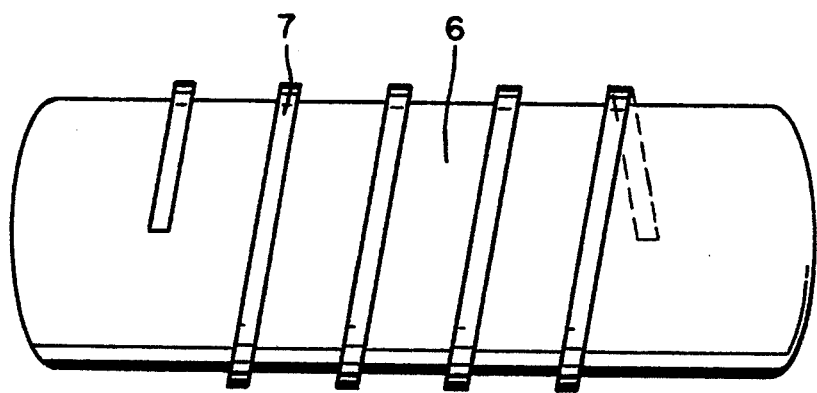
FIG. 6 is a side view of a shell assembly having spiral ridges thereon useable in the heart pump in accordance with the principles of the present invention.

As shown in FIGS. 1 and 6, the rotatable shell assembly 6 includes a spiral ridge thereon. By using different spiral ridge patterns on the shell assembly 6, the blood flow rate for a constant frequency of rotation may be varied. For example, a shell assembly 6 having a greater number of ridges per unit of axial length may tend to pump more blood than a shell assembly having fewer spiral ridges per unit of axial length at the same frequency. The spiral ridge, by rotation, causes the blood located in the area between the housing 2 and the shell assembly 6 to be displaced therethrough. Effect of the rotating spiral ridge is to avoid large pressure gradients such as those commonly exhibited across rotors and impellers. Blood cells which are displaced by the spiral ridge and rotating shell 6 are not exposed to large pressure gradients over a specific length of travel. The spiral ridge acts similar to a positive displacement apparatus rather than an impeller. Accordingly, the potential damage to blood cells due to explosive decompression and/or cavitation which may typically occur with the use of impellers and rotors is minimized.

Figure 4A:
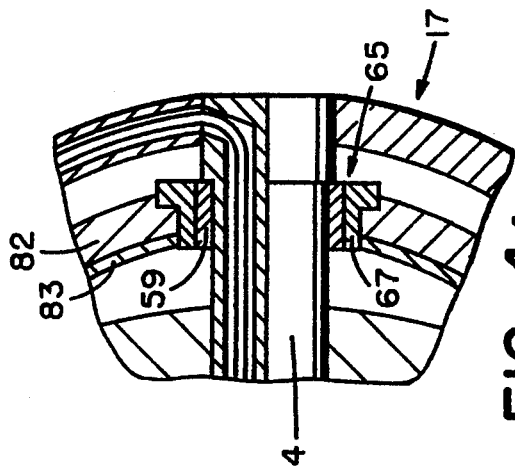
FIGS. 4 and 4A depict a perspective view and a sectional view, respectively, of a second jewel bearing useable within the heart pump constructed in accordance with principles of the present invention depicted in FIGS. 3 and 3A.
Figure 4B:
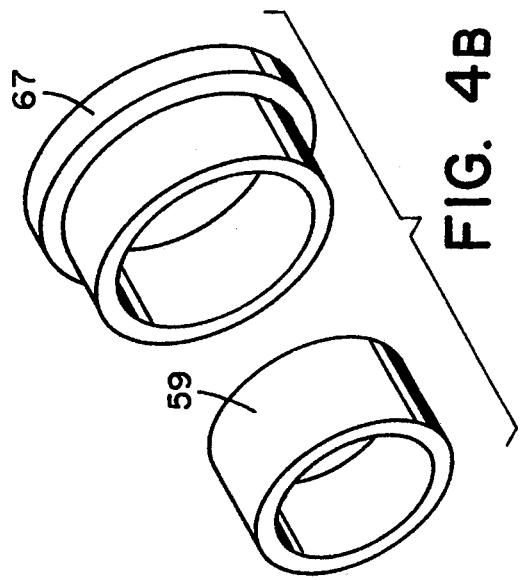
Figure 3A:
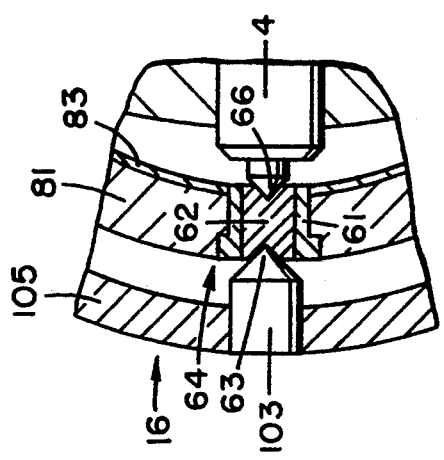
FIGS. 3 and 3A depict a perspective view and a sectional view, respectively, of a first jewel bearing useable within the heart pump constructed in accordance with the principles of the present invention.
Figure 3B:
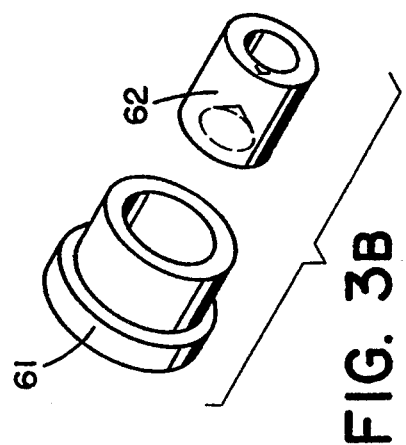

The ends 81, 82 of the shell assembly may contain first and second bearings 64, 65 therein which allow the shell assembly 6 to rotate relative to the shaft 4. The spiders 16, 17 may contain an outer ring (not shown) which is connected to an inner hub 103 by a plurality of ribs 105. The outer ring or the ribs 105 may be fastened within the housing 2 to maintain the spider 16 in position. Referring to FIGS. 3A and 3B, the first bearing 64 is mounted through the first end 61 of the rotatable shell 6 and engaged with the first end of the stationary shaft 4. The first bearing 64 contains a first jewel sleeve 61 and a jewel vee insert 62 therein. The jewel vee insert contains conical impressions therein which receive conical points 63, 66. Conical point 63 is fastened to the inner hub 103 of the first spider 16 while conical point 66 is affixed to stationary shaft 4 to allow the shell 6 to rotate. Referring to FIGS. 4A and 4B, the opposite end of the shaft 4 is inserted into second bearing 65 having a bearing sleeve 67 which is within a second sleeve 59 and affixed to an opening within the hub 103 of the second spider 17.

The three phases of current are supplied to the windings by three separate conductors 26, 27, 28 which pass through passage 22 from outside of the housing 2. The conductors may pass through an aperture in the housing which contains a seal therein to prevent blood leakage through the hole in the housing. When power is supplied to the windings 12, the configuration of the stator assembly 10, particularly the orientation of the windings 12, creates a first circumferential rotating magnetic flux wave. The permanent magnets within the rotatable shell assembly 6 also create a second circumferential magnetic flux wave which surrounds the first rotating flux wave created by the stator. The first rotating flux wave interacts with the second flux wave to rotate the shell assembly 6. The rotating spiral ridge 7 on the outside of shell assembly 6 will force blood through the housing 2. Blood may therefore flow in between the housing 2 and shell assembly 6 without interception or contact with a magnetic field.

Figure 7:
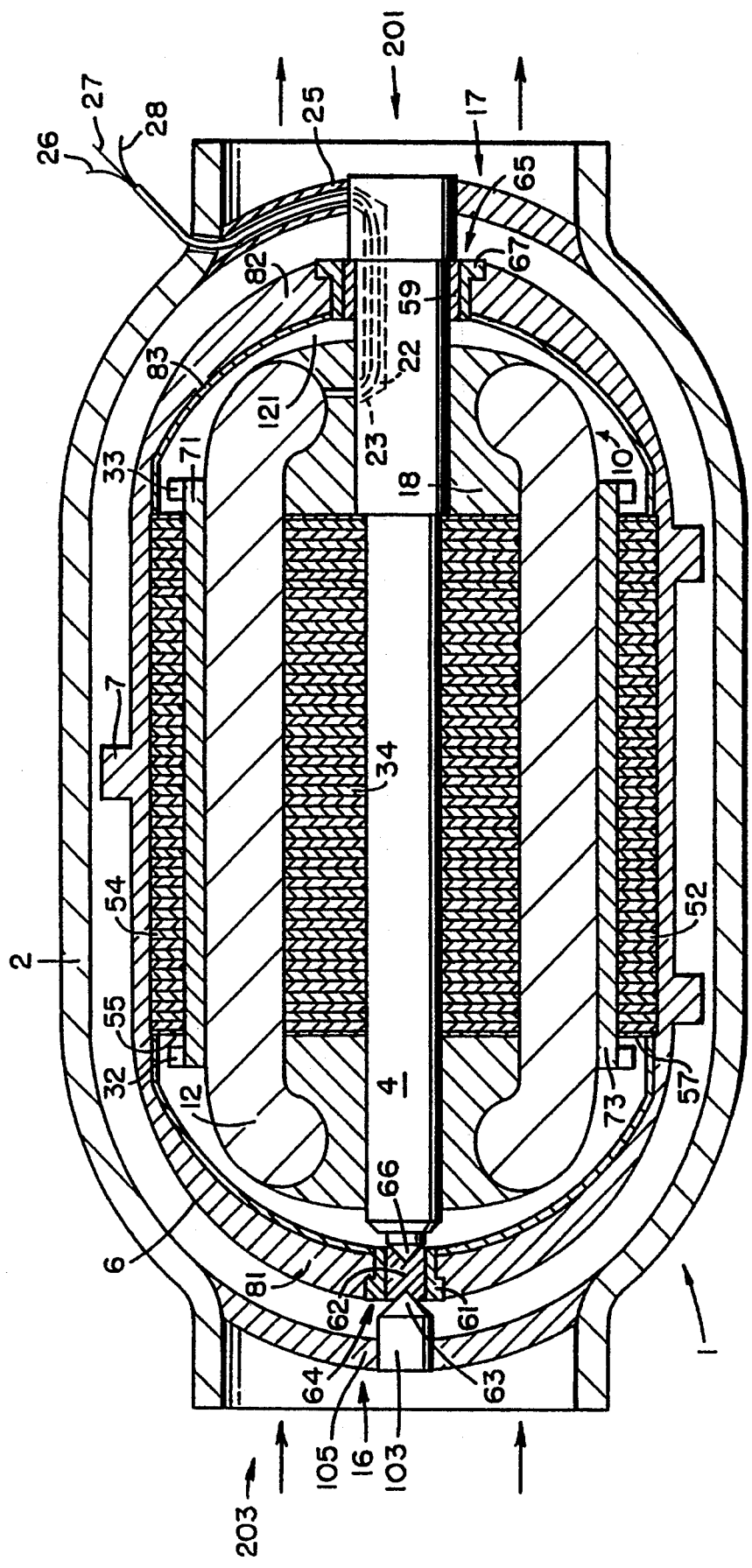
FIG. 7 depicts a cross-sectional view from the side of a second embodiment of the heart pump constructed in accordance with the principles of the present invention.

To facilitate eliminating the exposure of blood cells to magnetic fields, a flux shield 83 may be used to surround the area where the magnetic field exists. For example, referring to FIG. 1, the flux shield 83 may be placed all along an inner side of the shell assembly 6. As shown in FIG. 2, the flux shield may completely surround the rotor laminations 51, 52, 53, 54. The magnetic flux pattern within the pump, one portion of which is depicted by the arrows in FIG. 2, will not cross the flux shield. However, as shown in FIG. 7, the flux shield 83 may be placed solely at the shell assembly ends 81, 82, such that the flux shield 83 does not surround the rotor laminations 51, 52, 53, 54. The flux shield 83 is typically made of a magnetic shield material or a magnetically conductive material as is well known in the art. The flux shield 83 will prevent the magnetic field from entering into the area between the shell assembly 6 and the housing 2.

Since the heart pump utilizes multi-phase current, the effect of the electromagnetic fields created by conductors 26, 27 and 28 is minimal because the aggregate current through the conductors at a particular time is zero. Therefore, if the conductors are in close proximity to each other, such as if they are tied and twisted together, then the total current therethrough is zero and the electromagnetic fields created by the conductors 26, 27, 28 is minimal. To further minimize the effects of any electromagnetic fields, the conductors 26, 27, 28 may also be shielded.

The heart pump may be driven by an adjustable speed drive or a solid state inverter with adjustable speed capabilities. Using such a technique, the speed of rotation of the shell assembly 6 may be continuously adjusted to vary the pumping rate of the heart pump. By continuously adjusting the rotation of the shell assembly 6 between two selected speeds, a defined pulse rate, simulating a heart's actual pulse rate, may be obtained. The pump's rotational speed, and acceleration may be adjusted according to various physiological conditions including body temperature, blood pressure, pulse rate, metabolic rate, excitation, etc.

Referring again to FIG. 1, in order to facilitate blood to flow through the pump 1, surfaces which have contact with blood may be coated with a suitable monomolecular coating to prevent blood from adhering thereto. The area between the rotatable shell assembly 6 and the stator assembly 10 may also be filled with an inert fluid to help prevent blood from entering the area therebetween 121 and contacting the stator assembly 10.

Figure 8:
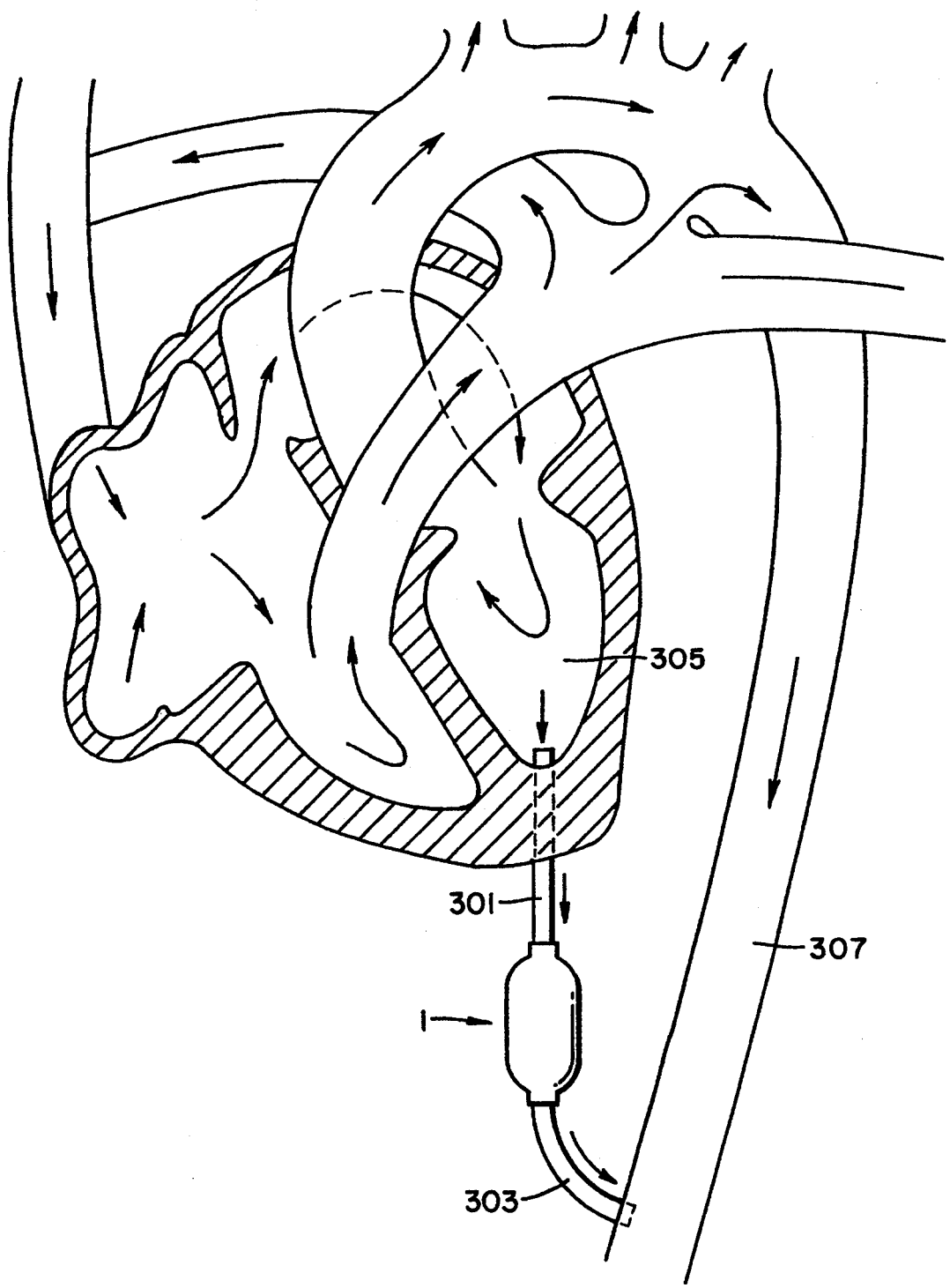
FIG. 8 depicts a representation of the heart pump in accordance with the principles of the present invention attached between the left ventricle of the heart and the aorta artery.

The heart pump may be, for example, mounted between the left ventricle 305 and aorta artery 307, as shown in FIG. 8, by suturing the vascular tissues 301, 303 thereto. However, insertion of the pump within the body is not limited to this position.

Although the invention has been described in connection with the embodiments depicted herein, it will be apparent to one skilled in the art that various modifications may be made to the invention without departing in any way, from the spirit of the invention. Any such modifications are intended to be within the scope of the invention as defined by the following claims.

What is claimed is:

1. A heart pump comprising:

a housing defining a central longitudinal axis therethrough, said housing having an inlet means and outlet means;

a stationary shaft extending axially within the housing;

means for supporting the shaft centrally within the housing;

a stator assembly mounted about the stationary shaft;

a shell assembly rotatable about the stator assembly and stationary shaft, said shell assembly being located between the housing and stator assembly and comprising means for pumping blood through the housing in an area between the housing and shell assembly; and means for generating a magnetic field using multi-phase current to rotate the shell assembly.

2. The heart pump of claim 1 wherein the means for generating a magnetic field generates a magnetic field between the stator assembly and shell assembly wherein the magnetic field does not cross the area between the shell assembly and housing where blood will flow therethrough.

3. The heart pump of claim 2 wherein the means for generating a magnetic field comprises:

a plurality of rotor laminations located on an inner side of the shell assembly, said rotor laminations having a plurality of axially extending permanent magnets therebetween, said permanent magnets being circumferentially spaced about the stationary shaft; and damper winding means mounted within the rotor laminations.

4. The heart pump of claim 3 wherein the stator assembly comprises a plurality of stator core laminations surrounding the stationary shaft, said stator core laminations forming a plurality of axially extending slots circumferentially spaced about the stationary shaft.

5. The heart pump of claim 4 wherein the stator assembly further comprises a plurality of stator windings located within the axially extending slots formed by the stator core laminations.

6. The heart pump of claim 5 wherein the axially extending permanent magnets circumferentially spaced about the stationary shaft have magnetic poles facing in a direction tangential to the circumference of the permanent magnets and wherein sides of adjacent permanent magnets oriented about the circumference facing each other have identical polarities.

7. The heart pump of claim 6 wherein the damper winding means comprises a plurality of damping bars, said bars extending axially within the rotor laminations and spaced circumferentially about the stationary shaft.

8. The heart pump of claim 7 wherein the damper winding means comprise at least one shorting ring circumferentially spaced about the stationary shaft and contacting the damping bars wherein the shorting rings and damping bars are in electrical conductive relationship.

9. The heart pump of claim 8 further comprising a plurality of damping slats circumferentially spaced about the stator assembly, the damping slats being located between the stator assembly and the permanent magnets, and further being in contact with at least one of the shorting rings.

10. The heart pump of claim 6 wherein the means for pumping blood comprises a spiral ridge located on an outerside of the shell assembly.

11. The heart pump of claim 6 further comprising means for supplying power to the stator assembly.

12. The heart pump of claim 11 wherein the means for supplying power to the stator assembly comprises a passage extending within the stationary shaft.

13. The heart pump of claim 12 wherein the stator windings receive three phase power thereto and wherein each of said windings contain one of three phases of power transmitted thereto.

14. The heart pump of claim 6 wherein the means for supporting the shaft centrally within the housing comprises at least one spider located between the housing and the shaft.

15. The heart pump of claim 6 further comprising flux shield within the shell assembly to restrict the magnetic field from entering the area between the housing and shell assembly where blood will flow.

16. The heart pump of claim 15 wherein the shell assembly is supported by a jewel bearing.

17. The heart pump of claim 6 wherein the pump is configured to be intravascularly mounted between a ventricle and an artery.

18. The heart pump of claim 17 wherein the pump is configured to be mounted between the left ventricle and the aorta artery.

19. A heart pump comprising:
- a housing defining a central longitudinal axis, said housing having an inlet means and outlet means;
- a stationary shaft centrally located and axially extending within the housing;
- at least one spider for supporting the shaft within the housing;
- a stator assembly having a plurality of stator core laminations surrounding the stationary shaft, the stator core laminations forming a plurality of axially extending slots circumferentially spaced about the stationary shaft, the stator assembly further comprising stator windings located within the axially extending slots formed by the stator core laminations;
- a shell assembly rotatable about the stator assembly and stationary shaft, said shell assembly being located between the housing and stator assembly and comprising a spiral ridge located on an outerside thereof for pumping blood through the housing between the housing and shell assembly as the shell assembly rotates;
- a plurality of rotor laminations located on an inner side of the shell assembly, the rotor laminations having a plurality of axially extending permanent magnets therebetween being circumferentially spaced about the stationary shaft, said axially extending permanent magnets having magnetic poles facing in a direction tangential to the circumference of the permanent magnets wherein the poles of the permanent magnets oriented about the circumference facing each other having identical polarities;
- a plurality of damping bars extending axially within the rotor laminations and spaced circumferentially about the stationary shaft;
- at least one shorting ring circumferentially spaced about the stationary shaft and contacting the damping bars wherein the shorting rings and damping bars are in electrical conductor relationship;
- a plurality of damping slats circumferentially spaced about the stator assembly and being located between the stator assembly and permanent magnets, said damping slats being in contact with the shorting rings;
- means for supplying power to the stator assembly, said means including a passage extending within the stationary shaft.

20. The heart pump of claim 19 wherein the stator windings receive three phase power thereto and wherein each of said stator windings contains one of three phases of power transmitted thereto.

21. The heart pump of claim 20 wherein the pump is configured to be intravascularly mounted between a ventricle and artery.

22. A heart pump comprising:
- a housing defining a central longitudinal axis therethrough, said housing having an inlet means and outlet means;
- a stationary shaft extending axially within the housing;
- means for supporting the shaft within the housing;
- a stator assembly mounted about the stationary shaft;
- a shell assembly rotatable about the stator assembly and stationary shaft, said shell assembly being located between the housing and stator assembly and comprising means for pumping blood through the housing between the housing and shell assembly as the shell assembly rotates;
- a plurality of rotor laminations located on an inner side of the shell assembly, said rotor laminations having a plurality of axially extending permanent magnets therebetween, said permanent magnets being circumferentially spaced about the stationary shaft; and
- damper winding means mounted within the rotor laminations.

* * * * *